United States Patent
Phadke et al.

(10) Patent No.: US 11,203,581 B2
(45) Date of Patent: Dec. 21, 2021

(54) HIGHLY PURIFIED PHARMACEUTICAL GRADE TASIMELTEON

(71) Applicant: VANDA PHARMACEUTICALS INC., Washington, DC (US)

(72) Inventors: Deepak Phadke, Olathe, KS (US); Natalie M. Platt, Columbia, MD (US); Ravi K. Pandrapragada, Clarksburg, MD (US)

(73) Assignee: VANDA PHARMACEUTICALS INC., Washington, DC (US)

(*) Notice: Subject to any disclaimer, the term of this patent is extended or adjusted under 35 U.S.C. 154(b) by 0 days.

(21) Appl. No.: 17/039,795

(22) Filed: Sep. 30, 2020

(65) Prior Publication Data

US 2021/0017143 A1  Jan. 21, 2021

Related U.S. Application Data

(63) Continuation of application No. 16/800,721, filed on Feb. 25, 2020, now Pat. No. 10,829,465, which is a continuation of application No. 16/123,303, filed on Sep. 6, 2018, now Pat. No. 10,611,744, which is a continuation of application No. 15/117,734, filed as application No. PCT/US2015/015564 on Feb. 12, 2015, now Pat. No. 10,071,977.

(60) Provisional application No. 61/938,932, filed on Feb. 12, 2014, provisional application No. 62/087,394, filed on Dec. 4, 2014.

(51) Int. Cl.
C07D 307/81 (2006.01)
C07D 307/79 (2006.01)

(52) U.S. Cl.
CPC ......... *C07D 307/81* (2013.01); *C07D 307/79* (2013.01)

(58) Field of Classification Search
CPC .................. C07D 307/81; C07D 307/79
See application file for complete search history.

(56) References Cited

U.S. PATENT DOCUMENTS

| | | | |
|---|---|---|---|
| 5,633,218 A | 5/1997 | Spedding | |
| 5,856,529 A | 1/1999 | Catt | C07D 317/58 549/469 |
| 2015/0329566 A1 | 11/2015 | Oosting | C07C 67/343 544/335 |

FOREIGN PATENT DOCUMENTS

| | | |
|---|---|---|
| CN | 103087019 | 5/2013 |
| CN | 103113177 | 5/2013 |
| JP | 2001505916 A | 5/2001 |
| WO | 98/25606 | 6/1998 |
| WO | 9825606 | 6/1998 |

OTHER PUBLICATIONS

Shekunov, B. Yu., & York, P., Crystallization Processes in Pharmaceutical Technology and Drug Delivery Design, 211 J. Crystal Growth 122-136 (2000) (Year: 2000).
FDA Guidance for Industry—Q3A Impurities in New Drug Substances, Jun. 2008, ICH (Year: 2008).
PCT/US2015/015564 International Search Report and Written Opinion dated Apr. 22, 2015.
"Guidance for Industry Q3A Impurities in New Drug Substances," U.S. Department of Health and Human Services Food and Drug Administration, Center for Drug Evaluation and Research, Center for Biologies Evaluation and Research, Revision 2, Jun. 2008, 17 pages.
Shekunov, "Crystallization Processes in Pharmaceutical Technology and Drug Delivery Design," Journal of Crystal Grownth, 211, Year 2000, pp. 122-136.
International Search Report and Written Opinion for Application No. PCT/US2015/015564, dated Apr. 22, 2015.
Pharm Tech Japan, vol. 18, No. 10, pp. 81-96 (pp. 16-29-16-44), Year 2002.
Pharmaceutical Affairs Bureau Notification No. 1216001, regarding the revision of the guideline for impurities in active pharmaceutical ingredients among novel active ingredient-containing pharmaceutical, Ministry of Health, Labour and Welfare, Dec. 16, 20012.
Notice of Reasons for Rejection for Japanese Application. 2016-552281, dated Oct. 15, 2018.

*Primary Examiner* — Timothy R Rozof
(74) *Attorney, Agent, or Firm* — Hoffman Warnick LLC

(57) ABSTRACT

A process for preparing a batch of highly purified, pharmaceutical grade tasimelteon comprises analyzing a batch of tasimelteon synthesized under GMP conditions for the presence of one or more identified impurities.

12 Claims, No Drawings

US 11,203,581 B2

HIGHLY PURIFIED PHARMACEUTICAL GRADE TASIMELTEON

CROSS-REFERENCE TO RELATED APPLICATIONS

This application claims the benefit of U.S. patent application Ser. No. 16/800,721, filed 25 Feb. 2020, now U.S. Pat. No. 10,829,465, which is a continuation of then U.S. patent application Ser. No. 16/123,303, filed 6 Sep. 2018, now U.S. Pat. No. 10,611,744, which is a continuation of then U.S. patent application Ser. No. 15/117,734, filed 10 Aug. 2016, now U.S. Pat. No. 10,071,977, which is the U.S. National Phase of PCT Application Serial No. PCT/US2015/015564, filed 12 Feb. 2015, which claimed the benefit of then U.S. Provisional Application Ser. No. 61/938,932, filed 12 Feb. 2014, and then U.S. Provisional Application Ser. No. 62/087,394, filed 4 Dec. 2014, each of which is incorporated herein as though fully set forth.

FIELD OF THE INVENTION

The disclosure relates generally to the synthesis of tasimelteon. In some embodiments, impurities, which may be by-products or degradation products, are analyzed and controlled in order to keep the impurities below pre-set specifications.

BACKGROUND OF THE INVENTION

Tasimelteon, N-(((1R,2R)-2-(2,3-dihydrobenzofuran-4-yl)cyclopropyl)methyl)-propionamide, is a melatonin agonist useful in the treatment of persons suffering from certain sleep-related disorders.

A synthesis of tasimelteon is disclosed, e.g., in Example 2 of U.S. Pat. No. 5,856,529. The end step synthesis in that example comprises reaction of ((1R,2R)-2-(2,3-dihydrobenzofuran-4-yl)cyclopropyl)methanamine with propionyl chloride. Synthesis of the methanamine intermediate is described in Preparation 24 and comprises reaction of ((1R,2R)-2-(2,3-dihydrobenzofuran-4-yl))cyclopropanecarboxaldehyde with hydroxylamine hydrochloride. Synthesis of the carboxaldehyde intermediate is described in Preparation 18 and comprises palladium catalyzed cyclization of a propenoyl intermediate, specifically, (1R,2R)-2-(2,3-dihydrobenzofuran-4-yl)propenoyl)-2,10-camphorsultam.

SUMMARY OF THE INVENTION

In one illustrative embodiment, the invention relates to a process for synthesizing highly purified, pharmaceutical grade tasimelteon, the process comprising:
  (a) propionylating ((1R,2R)-2-(2,3-dihydrobenzofuran-4-yl)cyclopropyl)methanamine or a salt thereof to yield tasimelteon;
  (b) crystallizing the tasimelteon produced in step (a);
  (c) assaying the crystallized tasimelteon from step (b) for the presence of one or both of Impurity 5 (N-((2-(2,3-dihydrobenzofuran-4-yl)-1-((2-(2,3-dihydrobenzofuran-4-yl)cyclopropyl)(propionamido)methyl) cyclopropyl)methyl)propionamide) and Impurity 6 (2-hydroxy-6-(2-(propionamidomethyl)cyclopropyl) phenethyl 2-(2-hydroxyethyl)-3-(2-(propionamidomethyl)cyclopropyl)phenyl carbonate); and
  (d)(i) if the crystallized tasimelteon meets pre-set specifications for Impurity 5 or Impurity 6, or both, then collecting the highly purified, pharmaceutical grade tasimelteon or
  (d)(ii) if the crystallized tasimelteon fails to meet pre-set specifications for Impurity 5 or Impurity 6, or both, then further purifying the tasimelteon and repeating steps (c) and (d), or discarding the batch.

In another illustrative embodiment, the invention relates to a process for preparing a batch of highly purified, pharmaceutical grade tasimelteon, the process comprising:
(a) analyzing a batch of tasimelteon synthesized under conditions of Good Manufacturing Practices ("GMP conditions") for the presence of an identified impurity(ies) that is(are) one or more of:
N-(((1R,2R)-2-(2,3-dihydrobenzofuran-4-yl)cyclopropyl)methyl)-3-methylbutanamide (Impurity 1),
N-(((1R,2R)-2-(2,3-dihydrobenzofuran-4-yl)cyclopropyl)methyl)-pentanamide (Impurity 2),
1,3-Bis(((1R,2R)-2-(2,3-dihydrobenzofuran-4-yl)cyclopropyl)methyl)urea (Impurity 3),
N-(((1R,2R)-2-(benzofuran-4-yl)cyclopropyl)methyl)propionamide (Impurity 4)
N-((2-(2,3-dihydrobenzofuran-4-yl)-1-((2-(2,3-dihydrobenzofuran-4-yl)cyclopropyl)(propionamido)methyl) cyclopropyl)methyl)propionamide (Impurity 5),
2-hydroxy-6-(2-(propionamidomethyl)cyclopropyl)phenethyl 2-(2-hydroxyethyl)-3-(2-(propionamidomethyl)cyclopropyl)phenyl carbonate (Impurity 6),
N-(((1R,2R)-2-(3-Oxo-2,3-dihydrobenzofuran-4-yl)cyclopropyl)methyl)propionamide (Impurity 7)
and
(b) if the batch meets pre-set specifications for the amount of the one or more of Impurity 1, Impurity 2, Impurity 3, Impurity 4, Impurity 5, Impurity 6, or Impurity 7, then continuing to process the tasimelteon to prepare bulk tasimelteon drug substance for formulation or
(c) if the tasimelteon does not meet said pre-set specifications, then further purifying (such as by recrystallization, trituration, extraction, or chromatography) the tasimelteon and repeating steps (a) and (b) or discarding the batch.

In another illustrative embodiments, further specifications for continuing to process the tasimelteon are pre-set, e.g., that the tasimelteon is not less than ("NLT") 95.0%, or NLT 98.0% pure (by area under the curve) and/or that the amount of any other single impurity is NMT 0.10 area %.

In another illustrative embodiment, the invention relates to a process for preparing a batch of tasimelteon drug product (i.e., tasimelteon plus excipients) wherein release of a batch of tasimelteon bulk drug substance for use in the manufacture of the tasimelteon drug product is contingent upon the testing and application of acceptance criteria for the amounts of one or more of the following impurities:
N-(((1R,2R)-2-(2,3-dihydrobenzofuran-4-yl)cyclopropyl)methyl)-3-methylbutanamide (Impurity 1),
N-(((1R,2R)-2-(2,3-dihydrobenzofuran-4-yl)cyclopropyl)methyl)-pentanamide (Impurity 2),
1,3-Bis(((1R,2R)-2-(2,3-dihydrobenzofuran-4-yl)cyclopropyl)methyl)urea (Impurity 3),
N-(((1R,2R)-2-(benzofuran-4-yl)cyclopropyl)methyl)propionamide (Impurity 4)
N-((2-(2,3-dihydrobenzofuran-4-yl)-1-((2-(2,3-dihydrobenzofuran-4-yl)cyclopropyl)(propionamido)methyl) cyclopropyl)methyl)propionamide (Impurity 5),
2-hydroxy-6-(2-(propionamidomethyl)cyclopropyl)phenethyl 2-(2-hydroxyethyl)-3-(2-(propionamidomethyl)cyclopropyl)phenyl carbonate (Impurity 6),
N-(((1R,2R)-2-(3-Oxo-2,3-dihydrobenzofuran-4-yl)cyclopropyl)methyl)propionamide (Impurity 7).

In a further illustrative embodiment, the invention relates to purified tasimelteon wherein the tasimelteon does not contain any of Impurities 1 through 7 at a concentration greater than about 0.15%. In related illustrative embodiments, such composition does not contain any related-substance impurity (i.e., an impurity that is structurally related to tasimelteon such as degradation products, dimers, etc.) at a concentration of greater than about 0.15% by weight.

DETAILED DESCRIPTION OF THE INVENTION

The synthesis of tasimelteon can result in a plurality of impurities following the end step synthesis. An illustrative synthesis of tasimelteon is a linear process, passing through a methanamine intermediate such as by the process described in U.S. Pat. No. 5,856,529 and involving four purification steps: one purification step for each of three isolated intermediates, as described below, as well as one for the unmilled tasimelteon drug substance. (1R,2R)-2-(2,3-dihydrobenzofuran-4-yl)cyclopropanecarboxylate (herein referred to as Intermediate 3 or Stage 9), (1R,2R)-2-(2,3-dihydrobenzofuran-4-yl)cyclopropane carboxamide (herein referred to as Intermediate 4 or Stage 10), and the methanamine intermediate (herein referred to as Intermediate 5 or Stage 11) and the tasimelteon (unmilled) drug substance are each isolated by crystallization and, if necessary, are subjected to recrystallization to improve purity.

The inventors have discovered that in the synthesis of tasimelteon there are certain impurities that can be formed as both by-products and degradation products, and that these impurities can be controlled or reduced to non-detectable or acceptably detectable levels. Although not desiring to be bound by theory, the inventors have identified some of these impurities on the basis of mass spectrometric, nuclear magnetic resonance spectroscopic and other data. The inventors have found that the impurities can include one or more of:
N-(((1R,2R)-2-(2,3-dihydrobenzofuran-4-yl)cyclopropyl) methyl)-3-methylbutanamide (Impurity 1),
N-(((1R,2R)-2-(2,3-dihydrobenzofuran-4-yl)cyclopropyl) methyl)-pentanamide (Impurity 2),
1,3-bis(((1R,2R)-2-(2,3-dihydrobenzofuran-4-yl)cyclopropyl)methyl)urea (Impurity 3),
N-(((1R,2R)-2-(benzofuran-4-yl)cyclopropyl)methyl)propionamide (Impurity 4),
N-((2-(2,3-dihydrobenzofuran-4-yl)-1-((2-(2,3-dihydrobenzofuran-4-yl)cyclopropyl)(propionamido)methyl) cyclopropyl)methyl)propionamide (Impurity 5),
2-hydroxy-6-(2-(propionamidomethyl)cyclopropyl)phenethyl 2-(2-hydroxyethyl)-3-(2-(propionamidomethyl)cyclopropyl)phenyl carbonate (Impurity 6), and
N-(((1R,2R)-2-(3-oxo-2,3-dihydrobenzofuran-4-yl)cyclopropyl)methyl)propionamide (Impurity 7).

Impurities 1-3 and 5-6 may be by-products of certain steps of the synthesis of tasimelteon, and impurities 4 and 7 may be degradation products.

The inventors have also found that in the synthesis of tasimelteon, there are certain additional impurities that can occur as degradation products, reaction byproducts, residual reagents, and residual intermediates. These additional impurities can be controlled or reduced to non-detectable or acceptably detectable levels. These impurities can include (+)-dehydroabietylamine, propionyl chloride, propionic acid, ethyl propionate [possibly additional potential degradants of propionyl chloride], ethyl diazoacetate, Intermediates 2, 4, and 5, 4-vinyl-2,3-dihydrobenzofuran (VBF), 4-(2-chloroethyl)-2,3-dihydrobenzofuran (VBF-int-2), benzene, and heavy metals such as As, Al, Fe, Li, Ni, Ru, Pd, Mn, Rh, Cu, and Co.

Some such impurities, such as ethyl diazoacetate and propionyl chloride, are potentially genotoxic and must be controlled to ppm levels in order for the bulk GMP tasimelteon to be suitable for formulation into bulk pharmaceutical composition and subsequently distributed into pharmaceutical dosage units.

The identification of such impurities facilitates quality control and consistency of product. With the knowledge of the identities of these impurities, a manufacturer of tasimelteon can set specifications for the maximum allowable amount of the impurities in bulk GMP tasimelteon, which can then be formulated into bulk pharmaceutical composition and then distributed into pharmaceutical dosage units.

Thus, in one aspect, this invention comprises a batch of pharmaceutical grade, highly purified tasimelteon that has been analyzed for the presence of any or each of these impurities and determined to have less than a pre-determined amount of one or more of them. The pre-determined amounts, i.e., the pre-set specifications, for these intermediates can be set to satisfy regulatory requirements. For example, the pre-set specification for Impurities 1-7 and the additional impurities can be 0.15 wt %. In a further embodiment, the pre-set specification can be 0.10 area %, e.g., for unidentified impurities. Additionally, a pre-set specification may include not more than (NMT) 100 ppm or NMT 10 ppm of ethyl diazoacetate (EDA)

The impurities are detectable by analytical chemical techniques such as chromatographic and mass spectrometry techniques among others. For example, HPLC, GC, or other chromatography methods can be used, in which case the amount of one or of each of the impurities can be determined on the basis of wt % or of area under the curve.

As used herein, abbreviations for methods and techniques may include: High-performance Liquid Chromatography (HPLC), Ultra Performance Liquid Chromatography (UPLC), Supercritical fluid chromatography (SFC), Gas chromatography (GC), Good Manufacturing Practices (GMP), Current Good Manufacturing Practices (cGMP), not more than (NMT), and not less than (NLT).

References herein to percent (%) purity are based on area. Such relative quantities approximate weight % but persons skilled in the art know how to determine more precise weight % amounts if desired.

A synthesis of tasimelteon is disclosed, e.g., in Example 2 of U.S. Pat. No. 5,856,529. The end step synthesis in that example comprises reaction of ((1R,2R)-2-(2,3-dihydrobenzofuran-4-yl)cyclopropyl)methanamine with propionyl chloride. Synthesis of the methanamine intermediate is described in Preparation 24 and comprises reaction of ((1R, 2R)-2-(2,3-dihydrobenzofuran-4-yl))cyclopropanecarboxaldehyde with hydroxylamine hydrochloride. Synthesis of the carboxaldehyde intermediate is described in Preparation 18 and comprises palladium catalyzed cyclization of a propenoyl intermediate, specifically, ((1R,2R)-2-(2,3-dihydrobenzofuran-4-yl)propenoyl)-2,10-camphorsultam.

An alternative route to the methanamine intermediate or a salt thereof (herein referred to as Intermediate 5) proceeds through (1R,2R)-2-(2,3-dihydrobenzofuran-4-yl)cyclopropanecarboxylate (Intermediate 3) to (1R,2R)-2-(2,3-dihydrobenzofuran-4-yl)cyclopropane-carboxamide (Intermediate 4) and then to Intermediate 5 or a salt thereof.

A synthesis of Intermediate 2 by stereoselective cyclization of 4-vinyl-2,3-dihydrobenzofuran is described, e.g., in U.S. Pat. No. 7,754,902.

An illustrative end-step synthesis of tasimelteon from Intermediate 5 is provided in Scheme 6, below. In general, the synthesis comprises:

(a) propionylating ((1R,2R)-2-(2,3-dihydrobenzofuran-4-yl)cyclopropyl)methanamine or a salt thereof to yield tasimelteon;

(b) crystallizing the tasimelteon produced in step (a);

(c) assaying the crystallized tasimelteon from step (b) for the presence of one or both of Impurity 5 (N-((2-(2,3-dihydrobenzofuran-4-yl)-1-((2-(2,3-dihydrobenzofuran-4-yl)cyclopropyl)(propionamido)methyl) cyclopropyl)methyl)propionamide) and Impurity 6 (2-hydroxy-6-(2-(propionamidomethyl)cyclopropyl) phenethyl 2-(2-hydroxyethyl)-3-(2-(propionamidomethyl)cyclopropyl)phenyl carbonate); and (d)(i) if the crystallized tasimelteon meets pre-set specifications for Impurity 5 or Impurity 6, or both, then collecting the highly purified, pharmaceutical grade tasimelteon or (d)(ii) if the crystallized tasimelteon fails to meet pre-set specifications for Impurity 5 or Impurity 6, or both, then further purifying the tasimelteon and repeating steps (c) and (d), or discarding the batch.

In such end-step synthesis, the propionylating step may comprise contacting ((1R,2R)-2-(2,3-dihydrobenzofuran-4-yl)cyclopropyl)methanamine or a salt thereof with a propionyl halide, a propionyl anhydride, a propionyl ester, a propionyl amide, a propionyl imidazolide, or with propionic acid and a dehydrating agent or the product thereof. Water is a byproduct of the coupling of ((1R,2R)-2-(2,3-dihydrobenzofuran-4-yl)cyclopropyl)methanamine with propionic acid to form tasimelteon. The dehydrating agent, which is also known as a peptide coupling reagent, is an agent that activates propionic acid toward reaction with ((1R,2R)-2-(2,3-dihydrobenzofuran-4-yl)cyclopropyl)methanamine and consumes the byproduct, water. Commonly used dehydrating agents include but are not limited to dicyclohexylcarbodiimide (DCC), DCC and an aminopyridine, N,N'-carbonyldiimidazole, chlorosilanes, Amberlyst-15, MeSO2Cl-Et3N, BF3, TiCl4, other Lewis acids, reagents of the type ArB(OH)2, Sn[N(TMS)2], POCl3, molecular sieves, Lawesson's reagent, and (MeO)2POCl.

The propionylation may be carried out in the presence of an organic solvent (e.g., ter-butyl methyl ether) and an aqueous base (e.g., NaOH). After the propionylation step and before the crystallizing step, the mixture of tasimelteon may be assayed for the presence of Intermediate 5 (or the free base or other salt thereof) and, if the mixture does not meet pre-set specifications for Intermediate 5 (e.g., not more than 0.15% or not more than 0.10%), then repeating step (a) or discarding the mixture. After the propionylation step and before the crystallizing step, the mixture of tasimelteon may be washed with aqueous base and the aqueous layer discarded, after which the washed mixture may be distilled (e.g., in ethanol at up to about 58° C., and less than about 100 mmHg). The crystallization step may comprise dissolving the tasimelteon by stirring and warming a mixture of the tasimelteon and a C1-C4 alkanol (e.g., about 35 to about 40° C.) and then cooling (e.g., to about 13 to about 17° C.) while stirring. The crystallization step optionally comprises seeding.

An illustrative synthesis of tasimelteon, in one embodiment, can include the following reaction schemes with a number of intermediates being synthesized first.

Synthesis of
4-(2-Chloroethyl)-2,3-dihydrobenzofuran
(VBF-int-2)

The synthesis of VBF-int-2 can comprise contacting and reacting 2,3-Bis(2-hydroxyethyl)phenol (Triol) with N,N-dimethylchloromethyleneiminium chloride (the Vilsmeier reagent) in an organic solvent, followed by reacting the resulting N,N'-[(3-hydroxy-1,2-phenylene)-bis(ethane-2,1-diyloxymethylidene)]-bis(N-methylmethanaminium) dichloride (VBF-int-1) with triethylamine in an organic solvent. The Vilsmeier reagent may be generated in situ from N,N-dimethylformamide (DMF) and oxalyl chloride. Said reaction is illustrated in the following scheme:

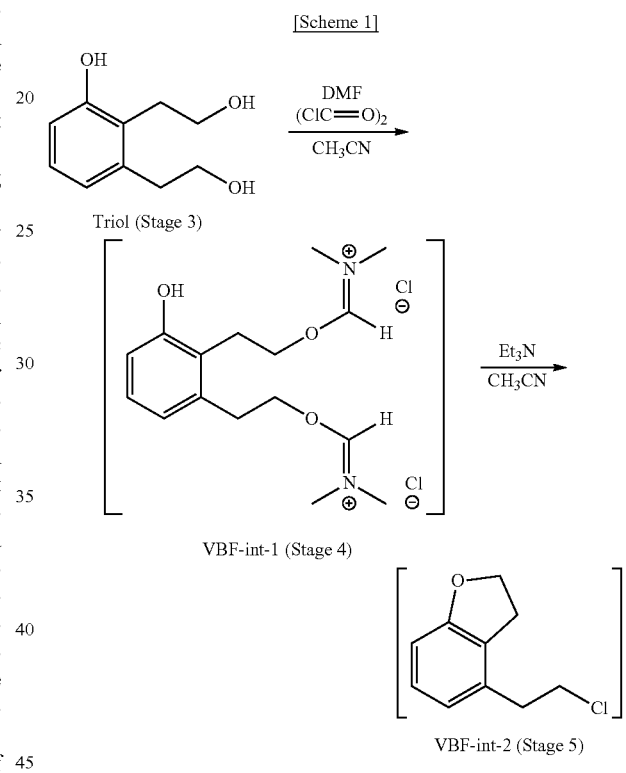

For example, a first reaction mixture can be prepared by slowly adding oxalyl chloride (approximately 2.45-2.55 equiv) to a solution of DMF (approximately 2.45-2.55 equiv) in CH3CN (Acetonitrile (e.g., 16% by weight DMF)) at −10±5° C. while maintaining the batch temperature at −10±5° C. Stirring may be continued at this temperature for approximately 30-40 min to complete the formation of the Vilsmeier reagent (N,Ndimethylchloromethyleneiminium chloride) in situ. Triol (Stage 3) (1.00 equiv; e.g., 30 kg) is added to the solution of the Vilsmeier reagent in portions through an addition funnel while maintaining the batch temperature at −10±5° C. Stirring is continued at about −20 to about −5° C. for at least 90 min, until testing via high pressure liquid chromatography (HPLC) indicates that no more than (NMT) 2.0% Triol (Stage 3) remains in solution. If necessary, the mixture can be sampled again at 150 min and tested again for Triol levels. Following this, a solution of Et3N (triethylamine (approximately 3.8-4.1 equiv)) in CH3CN (e.g., 47% by weight Et3N) may be slowly added to the reaction mixture while maintaining the batch temperature at −10±5° C. This step is an exothermic step. The total volume of CH$_3$CN should be approximately 5-17 L/kg of Triol (Stage 3) input, and in one embodiment may be 10 L/kg of Triol (Stage 3) input. When the addition is complete, the mixture may be heated to 55±5° C. for 3-3.5 hr. The mixture may then be cooled to 25±5° C. and stirred for up to four increments of up to approximately 1 hr each until HPLC indicates VBF-int-1 (Stage 4) NMT 2.0 area %. Tap water (e.g., 2.3 L/kg of Triol (Stage 3)) is then added to this reaction mixture, and stirring is continued for 30-40 min. The mixture is distilled at <100 torr and less than approximately 40° C. until no more organic distillate is collected. TBME (e.g., 5.6 kg/kg of triol (Stage 3)) and tap water (e.g., 3.2 L/kg of Triol (Stage 3)) are then added to the batch residue. The mixture is stirred for 30-40 min and settled for 30-40 min. The aqueous layer is removed. A solution of H$_3$PO$_4$ (8.5% by weight) in aqueous brine (e.g., 5 kg of H$_3$PO$_4$ solution/kg of Triol (Stage 3)) is slowly added to the remaining organic layer. This mixture can be stirred for 30-40 min and settled for 30-40 min. The aqueous layer is removed once more. The organic phase can be washed one or more times with tap water (e.g., 5 L/kg of Triol (Stage 3)), each time stirring for approximately 30-40 minutes, settling for approximately 30-40 min, and removing the aqueous layer. Following the washing with tap water, the organic layer is distilled at <100 torr and less than approximately 40° C. until no more distillate is collected. The batch residue is subjected to short path distillation at 0.1-4 torr. Any distillate boiling below 105° C. is discarded. The distillate boiling at 105-130° C. is subjected to HPLC analysis. Material meeting a pre-set specification, e.g., VBF-int-2 (Stage 5) present at not less than (NLT) 95.0%, is used directly in the next step.

Synthesis of 4-Vinyl-2,3-dihydrobenzofuran (VBF) (Stage 6)

The synthesis of VBF can comprise contacting and reacting 4-(2-Chloroethyl)-2,3-dihydrobenzofuran (VBF-int-2) with tetrabutylammonium hydroxide in the presence of organic solvent. Said reaction is illustrated in the following scheme:

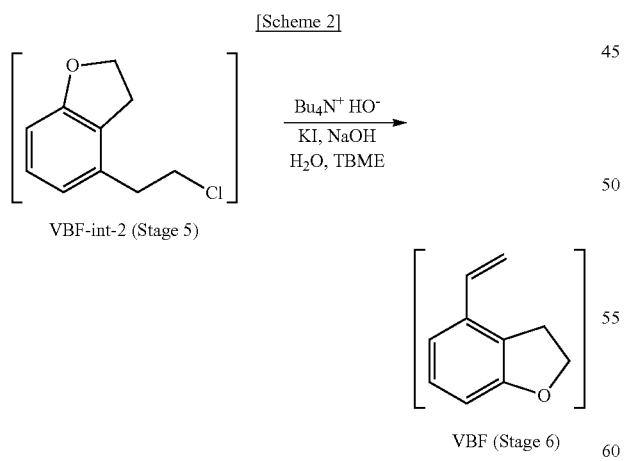

In one embodiment, tetrabutylammonium hydroxide (0.78 kg/kg of VBF-int-2 (Stage 5)), potassium iodide (0.09 kg/kg of VBF-int-2 (Stage 5)) and VBF-int-2 (from above (Stage 5)) is added to a mixture of TBME (tert-Butyl methyl ether) (5.60 kg/kg of VBFint-2 (Stage 5)) and 45% aqueous NaOH (4.80 kg/kg of VBF-int-2 (Stage 5)). In some embodiments, the NaOH, tetrabutylammonium hydroxide and KI charges are in the ranges 7-10, 0.15-0.50 and 0.08-0.10 molar equivalents, respectively. The mixture may be heated to 50±5° C. and stirred for approximately 3-3.5 hr. The mixture is then cooled to 25±5° C. and stirred for up to four increments of NLT 1 hr each until testing via HPLC indicates VBF-int-2 Stage 5) NMT 1.0%. The mixture is settled for 20-30 min and 40-60 L of the aqueous layer is discharged. 16% aqueous HCl (e.g., up to 6.2 kg/kg of VBFint-2 (Stage 5)) is added slowly to the remaining mixture until the pH of the mixture is 9.5-10.5. If necessary, 4.5% aqueous NaOH is added to adjust the pH into this range. The mixture can then be filtered using TBME (1 kg/kg of VBF-int-2 (Stage 5)) to complete the transfer and the filtrate settled for 20-30 minutes. The aqueous layer may then be removed. 8% Na$_2$S$_2$O$_3$ in 9% aqueous brine (e.g., 4.3 kg of Na$_2$S$_2$O$_3$ solution/kg of VBF-int-2 (Stage 5)) is added to the organic layer, then the mixture is stirred for 10-15 min and settled for 20-30 min and the aqueous layer is removed. To the organic layer is added 4% NaOH in 9% aqueous brine (e.g., 4.2 kg of NaOH solution/kg of VBF-int-2 (Stage 5)) followed by stirring, settling and removal of the aqueous layer. Then quinol (e.g., 7 g/kg of VBF-int-2 (Stage 5), or 1 mol %) is added to the organic layer and the mixture is stirred for 20-30 min. The resulting solution is subjected to HPLC analysis for purity and assay. Material meeting pre-set purity specification, e.g., VBF (Stage 6) NLT 95.0 area %, is used directly in the next step. The assay result from HPLC is reported as % wt/wt.

Synthesis of (1R,2R)-2-(2,3-Dihydrobenzofuran-4-yl) (Intermediate 3) (Stage 9)

The synthesis of Intermediate 3 (Stage 9) can comprise asymmetric cyclopropanation of 4-vinyl-2,3-dihydrobenzofuran (VBF (Stage 6)) by contacting and reacting it with EDA in the presence of a chiral catalyst. It can also comprise hydrolysis of the ester group of 2-(2,3-dihydrobenzofuran-4-yl)-cyclopropanecarboxylic acid ethyl ester (VEC-int-1 (Stage 7)) followed by polishing resolution of 2-(2,3-dihydrobenzofuran-4-yl)-cyclopropanecarboxylic acid (Intermediate 2 (Stage 8)) with (+)-dehydroabietylamine (DAA) in an organic solvent. Said reaction sequence is illustrated in the following scheme:

[Scheme 3]

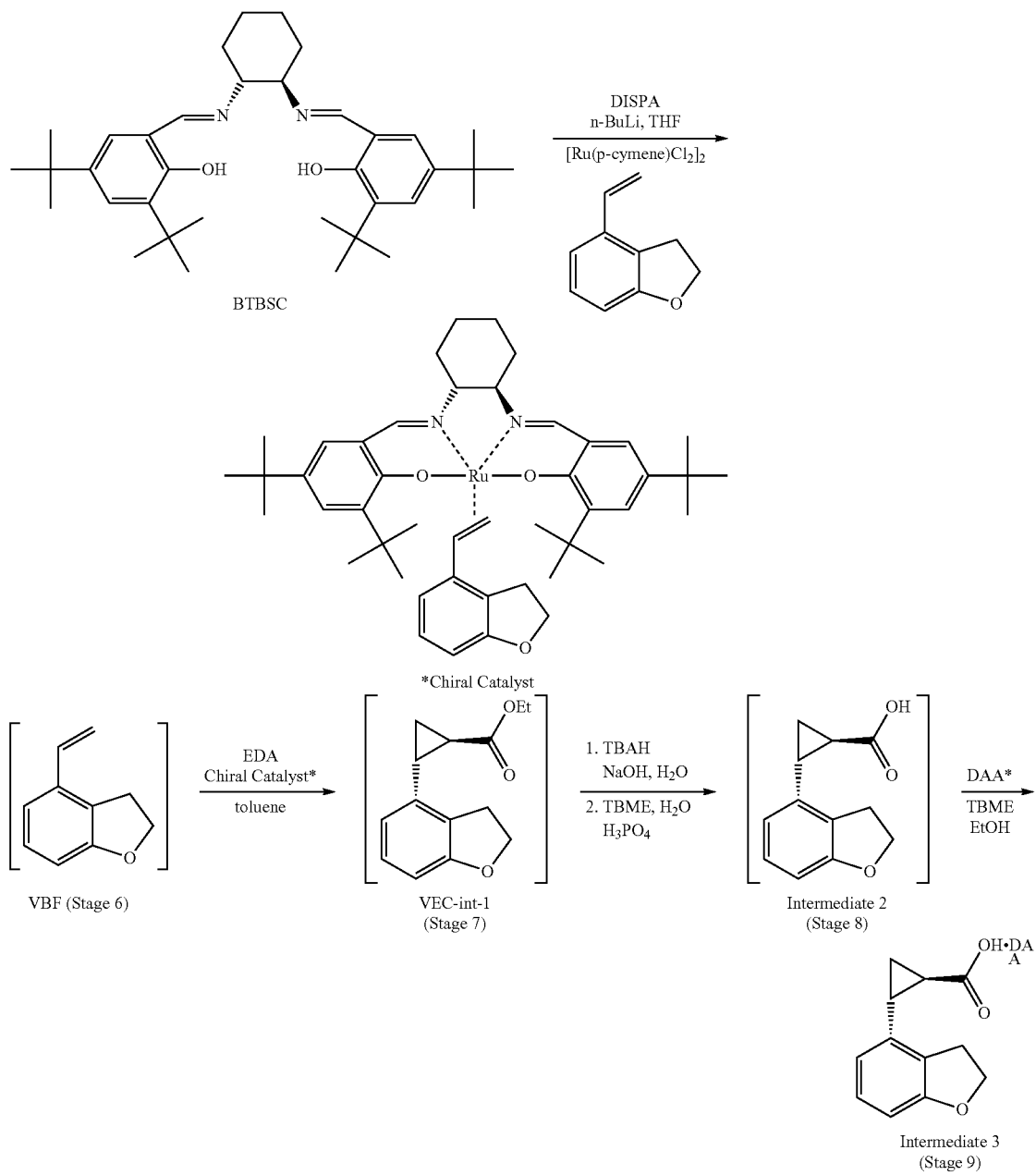

In one embodiment, in order to form Intermediate 3, a number of processes may be utilized in preparation.

A lithium diisopropylamide (LDA) solution may be prepared. For instance, a solution of n-butyllithium (0.03 equiv; 1 M in hexanes) is added, slowly, to a solution of diisopropylamine (DISPA; 0.04 equiv; e.g., 10 M) in THF at 5±5° C. After the addition is complete, stirring is continued at 5±5° C. for 30-40 min. The resulting solution of lithium diisopropylamide (LDA) is used directly for the subsequent deprotonation of BTBSC ((R,R)-(−)-N,N'-Bis(3,5-di-tert-butylsalicylidene)-1,2 cyclohexanediamine), as further described below.

A Ru catalyst may be prepared from BTBSC and the LDA solution. For instance, the preparation can comprise stirring a mixture of BTBSC (0.02 equiv; e.g., 0.04 M) in THF (tetrahydrofuran) at 25±5° C. for 30-40 min, and then cooling the mixture to 5±5° C. The LDA solution from above may then be added slowly to this mixture at 5±5° C. and the mixture stirred for approximately 60 min. To the resulting mixture is added, in portions, [Ru(pcymene)Cl$_2$]$_2$ (0.02 equiv, assuming 2 equiv Ru/mole of [Ru(p-cymene)Cl$_2$]$_2$). The reactor is purged three times with N$_2$. The mixture is stirred at 25±5° C. for 30-40 min. Lastly, VBF (Stage 6) solution (ca. 0.01 equiv) in TBME is added to this mixture. The resulting mixture is stirred at 20-25° C. for at least approximately 8 hours. The resulting Ru catalyst mixture is used directly in the subsequent cyclopropanation of VBF step.

VBF (Stage 6) may undergo cyclopropanation. For instance, in one embodiment, such a preparation may comprise adding toluene (e.g., 20 kg) to the VBF (Stage 6) solution (1.00 equiv) prepared as described for the preceding step in TBME (e.g., weight of solution (kg)=8.9/assay %) and distilling the mixture at <100 torr and <50° C. until about 20 L of residue remains in the reaction vessel. Toluene (e.g., 60 L) is added, and the mixture is again distilled at <100 torr and <50° C. until about 20 L of residue remains in the reaction vessel. The batch residue is cooled to 30±2° C., and the Ru catalyst prepared above is added. The Ru catalyst charge can include an amount of approximately 0.02 molar equivalents. To this mixture is added a solution of EDA in toluene over 8-16 hr at 30±2° C. The ethyl diazoacetate charge can include approximately 2.5 molar equivalents. The mixture is stirred for at least approximately 3 hr at 30±2° C. after the addition is complete. Material for which UPLC analysis shows NMT approximately 2.0% VBF (Stage 6) is used directly in the next preparation step, described in further detail below.

VEC-int-1 (Stage 7) may undergo a saponification. An illustrative example may include adding 45% aqueous NaOH (4 equiv), 55% aqueous tetrabutylammonium hydroxide (TBAH; 0.45 equiv) and tap water (e.g., 10 L) to the final reaction mixture from the cyclopropanation of VBF. This mixture is then stirred at 50-70° C. for 16-18 hr until HPLC indicates <2.0% VEC-int-1 (Stage 7). If the limit is not met, stirring is continued at 50-70° C. for 2-4 hr and the analysis is repeated. Once the limit is met, the mixture is cooled to 25-30° C. Tap water (e.g., 60.0 L) is added and the mixture is stirred for at least approximately 30 min, and settled for 30-40 min. The organic layer is discarded. TBME (e.g., 107.0 kg) is added to the resulting aqueous layer and the mixture is cooled to 0-10° C. Phosphoric acid (85% aqueous, e.g., 24.0 kg) is added slowly at 0-25° C. until the pH of the aqueous layer is 4.0-4.5. If necessary, 10% aqueous NaOH is added to bring the pH into this range. The mixture is then stirred for at least approximately 30 min and settled for another 30-40 min, the aqueous layer being discarded. Tap water (e.g., 70.0 L) is added and the mixture is stirred for at least approximately 30 min and settled again for approximately 30-40 min, and the aqueous layer is discarded. This tap water wash may be repeated, for instance three more washes may be utilized.

Lastly, the Intermediate 3 (Stage 9) (DAA salt) may be formed. In an illustrative example, TBME (e.g., 22.9 kg/kg of VBF (Stage 6)) and ethanol (EtOH; anhydrous, e.g., 4.49 kg/kg of VBF (Stage 6) may be added to the resulting organic layer from the saponification preparation step above. The ratio of Intermediate 2 (Stage 8) to TBME may be included in a range of 0.040-0.079 kg Intermediate 2 (Stage 8)/L TBME, and in a further embodiment may comprise a set point of 0.040 kg Intermediate 2 (Stage 8)/L TBME. In one embodiment, the ratio of TBME (kg):EtOH (kg) may be 7.78-9.08, and in a further embodiment may be 7.78. Next, (+)-dehydroabietylamine (1.44 equiv) as a 28% wt/wt solution in TBME may be added to the resulting mixture. In one embodiment, the (+)-dehydroabietylamine charge may be 1.44-1.76 molar equivalents, and in a further embodiment may be 1.44 molar equivalents. This reaction mixture may be heated to 45-55° C. and stirred for NLT 20 min, cooled to 25-30° C. in a period of NLT 2 hr and stirred at this temperature for NLT 1 hr, heated to 45-55° C. and stirred for NLT 20 min, cooled to 15-25° C. in a period of NLT 2 hr and stirred for NLT 4 hr, cooled to 0-5° C. in a period of NLT 1 hr and stirred for NLT 1 hr, and the precipitated solid is collected by centrifugation, washed with TBME, and spun, e.g., at full speed for 20±5 min. The collected wet cake is added to ethanol (anhydrous, e.g., 11.2 kg/kg of VBF (Stage 6)) that has been cooled to 0-5° C. The mixture is stirred at this temperature for 30-40 min and then centrifuged, e.g., at full speed for 20±5 min. This washed wet cake is subjected to purity analysis by HPLC. Material meeting pre-set specifications, e.g., (R,R)-trans-Intermediate 3 (Stage 9) NLT 99.0 area % and total impurities NMT 2.0%, is dried at NMT 80 torr and 60±5° C. for NLT 12 hr until loss on drying (LOD) meets a pre-set specification e.g., LOD NMT 2.0%. Material failing this specification is dried further at NMT 80 torr and 60±5° C. for NLT 6 hr and re-sampled.

Material meeting the specification is released. If the wet cake fails the purity test, it is processed again. The second process may comprise adding the wet cake to a cooled (e.g., 0-10° C.) mixture of 45% aqueous NaOH (e.g., 3.60 kg/kg of VBF (Stage 6)), tap water (e.g., 11.9 kg/kg of VBF (Stage 6)) and toluene (e.g., 4.49 kg/kg of VBF (Stage 6)), stirring for about 30 min, settling for about 30 min, and phase separation. To the aqueous layer is added TBME (e.g., 12.0 kg/kg of VBF (Stage 6)) and the mixture is cooled (e.g., to 0-10° C.). The pH of the aqueous layer is adjusted with phosphoric acid (85% aqueous, e.g., 24.0 kg) and, if necessary, 10% aqueous NaOH to a value of 4.0-4.5. After thorough mixing and settling, the layers are separated, and the organic phase is washed several times with tap water. Formation, isolation, drying and LOD and purity analysis of the Intermediate 3 (Stage 9) DAA salt is repeated as described above. Material meeting the specification is released.

Synthesis of (1R,2R)-2-(2,3-dihydrobenzofuran-4-yl)cyclopropanecarboxamide (Intermediate 4) (Stage 10)

The synthesis of Intermediate 4 can comprise liberation of the free carboxylic acid from (1R,2R)-2-(2,3-dihydrobenzofuran-4-yl) cyclopropanecarboxylic acid (+)-dehydroabietylamine salt (Intermediate 3) followed by conversion via the corresponding acid chloride to the amide, (1R,2R)-2-(2, 3-dihydrobenzofuran-4-yl)cyclopropane-carboxamide (Intermediate 4 (Stage 10)). Said reaction sequence is illustrated in the following scheme:

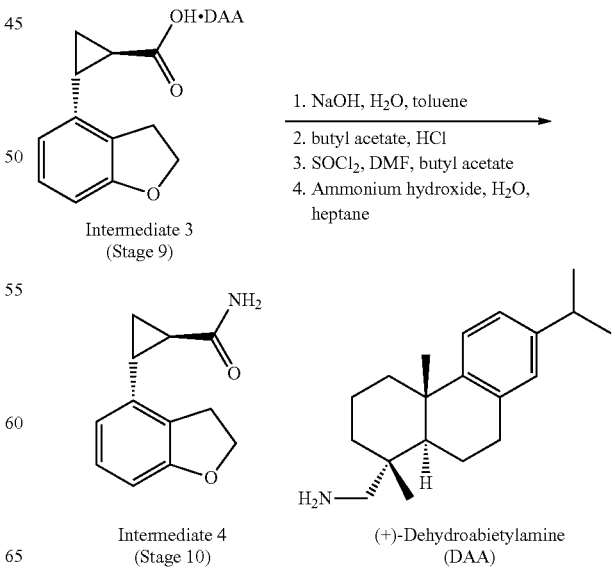

[Scheme 4]

Intermediate 3 (Stage 9)

1. NaOH, H₂O, toluene
2. butyl acetate, HCl
3. SOCl₂, DMF, butyl acetate
4. Ammonium hydroxide, H₂O, heptane Intermediate 4 (Stage 10)

(+)-Dehydroabietylamine (DAA)

In an illustrative example, Intermediate 4 may be synthesized by adding Intermediate 3 (Stage 9) (1 equiv, e.g., 20.0-21.0 kg) to a first reaction mixture of tap water (e.g., 5.2 L/kg of Intermediate 3 (Stage 9)), 45% aqueous NaOH (4 equiv), and toluene (e.g., 1.8 kg/kg of Intermediate 3 (Stage 9)) at 20-30° C. The mixture is then stirred at 25-30° C. for NLT 30 min and settled for 30-40 min, and the organic layer discarded. Toluene (e.g., 1.8 kg/kg of Intermediate 3 (Stage 9)) is added to the aqueous layer, followed by stirring for NLT 60 min, settling for 30-40 min and discarding the organic layer. The toluene wash can be repeated. Next, sodium chloride (e.g., 0.3 kg/kg of Intermediate 3 (Stage 9)) is added to the remaining aqueous layer. The temperature is adjusted to 15-20° C. Butyl acetate (e.g., 1.2 kg/kg of Intermediate 3 (Stage 9)) is added. Hydrochloric acid (32% aqueous, 2.9 equiv) is added slowly. The temperature is maintained at 15-20° C. while the mixture is stirred for NLT 60 min and settled for 30-40 min. If the pH of the aqueous layer is more than 3, additional 32% HCl is added until the pH is less than 3. The layers are separated, and the organic layer is set aside for later use. The aqueous layer is added to butyl acetate (e.g., 1.1 kg/kg of Intermediate 3 (Stage 9)). The temperature is maintained at 15-20° C. while the mixture is stirred for NLT 60 min and settled for 30-40 min. The aqueous layer is discarded. The organic layers are combined and distilled at <100 torr and a pot temperature of NMT 82° C. until the batch residue is about 30 L. The distillate is discarded. Butyl acetate (e.g., 0.71 kg/kg of Intermediate 3 (Stage 9)) is added to the batch residue. This mixture is distilled at <100 torr and a pot temperature of NMT 82° C. until the batch residue is about 30 L. The distillate is discarded. This step is repeated one or two more times until Karl Fischer moisture analysis indicates a value of less than approximately 0.1%. The batch residue is cooled to 15-20° C. DMF (0.03 equiv) and thionyl chloride (1.3 equiv) are added. The mixture is heated to 50-55° C., stirred for 1.5-2.0 hr and cooled to 21±4° C., and analyzed by HPLC. Material meeting pre-set specifications, e.g., Intermediate 2 (Stage 8) NMT 1.0%, is further processed. If this specification is not met, additional thionyl chloride (0.12 equiv) is added, and the mixture is heated to 50-55° C., stirred for 1.5-2.0 hr, cooled to 21±4° C., and re-sampled. Following this, a mixture of ammonium hydroxide (9.0 equiv) and tap water (e.g., 0.8 L/kg of Intermediate 3 (Stage 9)) is cooled to 0-5° C. The acid chloride solution from the previous step meeting the pre-set specification is added in portions while maintaining the batch temperature at 0-10° C. After the addition, stirring is continued for 30-40 min at 0-10° C. Then n-Heptane (e.g., 1.3 kg/kg of Intermediate 3 (Stage 9)) is added, and stirring is continued for 2-3 hr at 0-10° C. The resulting precipitate is collected by centrifugation. The wet cake is washed in the centrifuge cart with tap water (e.g., 15 L/cart) and then spun at full speed for 20±5 min. This wet cake is added to a mixture of butyl acetate (e.g., 0.71 kg/kg of Intermediate 3 (Stage 9)) and n-heptane (e.g., 0.3 kg/kg of Intermediate 3 (Stage 9)) at 0-10° C. The resulting mixture is stirred for 30-40 min at 0-10° C. and then centrifuged at full speed for 20±5 min. The wet cake is analyzed by HPLC to determine if pre-set specifications are met, e.g., Intermediate 4 (Stage 10) NLT 98.0%. If this specification is not met, the wet cake can be added to another mixture of butyl acetate and n-heptane, the stirring and centrifugation repeated until the wet cake meets the specification as analyzed by HPLC, e.g., Intermediate 4 (Stage 10) NLT 98.0%. The wet cake that meets the pre-set specifications is dried at NMT 80 torr and 45±5° C. for NLT 12 hr until pre-set specifications are met, e.g., LOD is NMT 1.0% and moisture by Karl Fischer analysis is NMT 0.2%. Material failing these pre-set specifications is dried further at NMT 80 torr and 45±5° C. for NLT 6 hr and resampled. Material meeting the pre-set specifications is released as Intermediate 4 (Stage 10), which may be stored in one or more polyethylene (PE) bags, which may also be sealed within a paper drum.

Synthesis of ((1R,2R)-2-(2,3-dihydrobenzofuran-4-yl)cyclopropyl)methanaminium chloride (Intermediate 5)

The synthesis of Intermediate 5 can comprise contacting and reacting (1R,2R)-2-(2,3-dihydrobenzofuran-4-yl)cyclopropanecarboxamide (Intermediate 4) with Lithium aluminum hydride in an organic solvent, followed by aqueous workup and isolation of the resulting amine as its hydrochloride salt. Said reaction is illustrated in the following scheme:

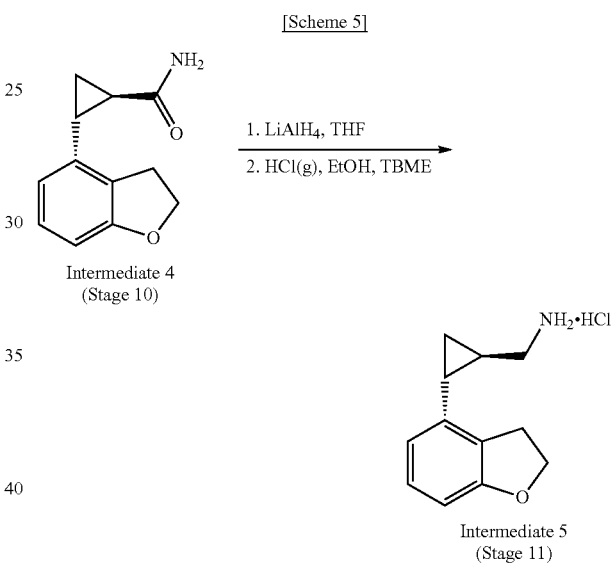

In one example, Intermediate 5 (Stage 11) may be synthesized by the above scheme, wherein the synthesis may include the following procedure. For example, a reactor (e.g., SS316) is cleaned with refluxing acetone (e.g., 100 kg), drained, dried under vacuum for 1-2 hr, and filled with $N_2$ gas. The Intermediate 4 (Stage 10) (1.00 equiv) made above and THF (e.g., 8 kg/kg of Intermediate 4 (Stage 10)) are added to the dry reactor and cooled to −10° C. Lithium aluminum hydride (LAH) solution (10% in THF, 3.5-3.8 equiv, where 1 equiv=1 mol/mol of Intermediate 4 (Stage 10)) is added in portions while keeping the batch temperature NMT 25° C. The LAH feed line is rinsed with THF (e.g., 10 kg). The mixture is warmed to 20-30° C. and stirred for 20-30 min. The mixture is then warmed slowly to 65-70° C. while maintaining an internal pressure of NMT 0.1 $kg/cm_2$. This mixture is stirred at 65-70° C. for 3-4 hr, cooled to 15-25° C., and analyzed by HPLC to determine if pre-set specifications are met, e.g., Intermediate 4 (Stage 10) NMT 1.0%. If this limit is not met, the previous warming and cooling whilst stirring is repeated. Upon HPLC indicating that not more than approximately 1.0% of Intermediate 4 remains, the reaction mixture is cooled to −5~5° C. Aqueous THF (91%, e.g., 1.09 kg/kg of 10% LAH) is added at NMT 25° C., and stirring is continued for 20-30 min. The water charge (as aqueous THF) may be 1.0-1.1 L of water/kg of LAH, and in a further embodiment may be 1.1 L of water/kg of LAH. Aqueous NaOH (5.3%, e.g., 0.37 kg/kg of 10% LAH) is added at NMT 25° C. (causing an exothermic reaction), and stirring is continued for 20-30 min. The NaOH charge may be 0.17-0.19 mol/mol of LAH, and in a further embodiment may be 0.18-0.19 mol/mol of LAH. The mixture is warmed slowly to 65-70° C., stirred for 3-4 hr, and cooled to 15-25° C. The mixture is filtered, using THF (e.g., 30 kg) to complete the transfer of the reaction mixture into the filter. The filtrate is kept in the receiver. This filter cake is then transferred back to the reactor and resuspended in fresh THF (1.3 kg/kg of 10% LAH). The mixture is stirred at 15-25° C. for 1-1.5 hr, and then filtered, using THF (0.65 kg/kg of 10% LAH) to complete the transfer again. The wet cake is discarded. The combined filtrates are distilled at <100 torr and NMT 40° C. until the batch residue is about 40 L. The distillate is discarded. TBME (e.g., 30 kg) is added to the remaining batch residue and the mixture is distilled at <100 torr and NMT 40° C. until the batch residue is about 40 L. The distillate is discarded. TBME (e.g., 20 kg) and tap water (e.g., 20 kg) are then added to the batch residue and the mixture is stirred for 60-70 min at 15-20° C. and settled for 30-40 min. The aqueous layer is discarded. Tap water (e.g., 20 kg) is then added to the organic layer and the mixture is stirred for 60-70 min at 15-20° C. and settled for 30-40 min. The aqueous layer is discarded. The organic layer is analyzed by inductively coupled plasma—optical emission spectroscopy to determine if pre-set specifications are met, e.g., Li NMT 10 ppm, Al NMT 10 ppm. If these specifications are not met, the wash with tap water is repeated until the specifications are met. Following meeting the specifications, anhydrous ethanol (e.g., 30 kg) is added to the organic layer meeting the specifications and the mixture is distilled at <100 torr and a pot temperature of NMT 40° C. until the batch residue is about 40 L. The distillate is discarded. Anhydrous ethanol (e.g., 82.8 kg) is added to the residue and the mixture is again distilled at <100 torr and a pot temperature of NMT 40° C. until the batch residue is about 40 L. The distillate is discarded. This azeotropic distillation step may be repeated one or two more times until pre-set specifications are met, e.g., Karl Fischer moisture analysis indicates a value of NMT 0.5%. The batch residue is then cooled to 15-25° C. and TBME ((tert-butyl methyl ether) e.g., 13.8 kg/kg of Intermediate 4 (Stage 10)) is added to the residue. The mixture is cooled to 0-5° C. Hydrogen chloride (HCl) gas (3.3 equiv) is added in portions at NMT 25° C., and stirring is continued for 60-70 min at 20-25° C. after the addition is complete. If the pre-set specification, e.g., pH NMT 1.0, is not met, more HCl gas is added until the specification is met. The resulting precipitate is collected by centrifugation. The wet cake is washed in the centrifuge cart with TBME:EtOH (anhydrous, 1.5:1.0, e.g., 5.0 kg), and the cake is centrifuged at full speed for 20±5 min. The cake is analyzed by HPLC to determine if pre-set specifications are met, e.g., Intermediate 5 (Stage 11) NLT 98.0%. If this specification is not met, the cake can be re-suspended in TBME:EtOH (anhydrous, 1.5:1.0, e.g., 6.6 kg/kg of Intermediate 4 (Stage 10)), and centrifuged and washed as above until the specification is met. The cake that meets the specification is dried at NMT 80 torr and 35±5° C. for NLT 12 hr until LOD is NMT 1.0%. Material which does not meet pre-set specifications is dried further at NMT 80 torr and 35±5° C. for NLT 6 hr and re-sampled. Material meeting the pre-set specifications is released as Intermediate 5 (Stage 11). The resulting Intermediate 5 (Stage 11) may be stored in one or more PE bags, which may in turn be sealed in a paper drum.

Synthesis of N-(((1R,2R)-2-(2,3-dihydrobenzofuran-4-yl)cyclopropyl)-methyl)propionamide (tasimelteon, Pre-Particle Size Reduction (i.e., Unmilled))

Following the synthesis of the above disclosed intermediates, tasimelteon, which is unmilled, may be synthesized. The end step synthesis of tasimelteon can comprise contacting and reacting ((1R,2R)-2-(2,3-dihydrobenzofuran-4-yl)cyclopropyl)methanaminium chloride (Intermediate 5) with propionyl chloride in the presence of organic solvent and base. Said reaction is illustrated in the following scheme:

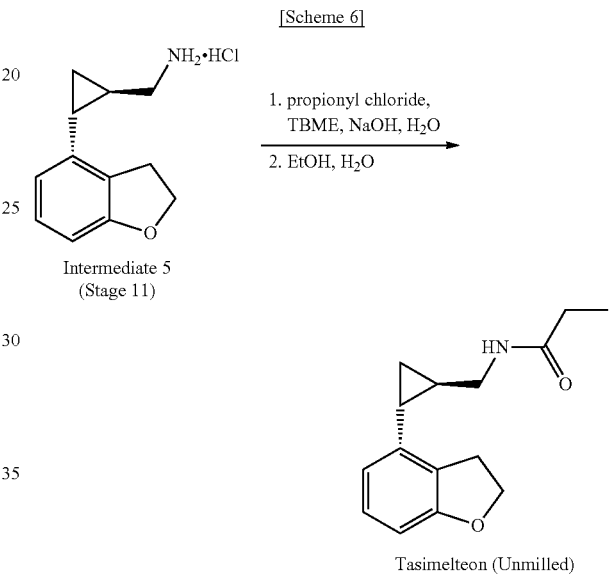

For example, in an illustrative end step synthesis, a first reaction mixture is prepared by adding 45% aqueous NaOH (8 equiv) to a mixture of Intermediate 5 (Stage 11, 1.00 equiv), TBME (e.g., 15.2 kg/kg of Intermediate 5 (Stage 11)) and tap water (e.g., 14.6 kg/kg of Intermediate 5 (Stage 11)) at 0-10° C. Propionyl chloride (1.28-1.46 equiv) is added at 5-10° C., after which the mixture is stirred at this temperature for 90-120 min. This mixture can be analyzed by HPLC to determine if the resultant solution meets pre-set specifications, e.g., Intermediate 5 (Stage 11) NMT 0.10%. After stirring and then settling, at 25-30 C, the aqueous layer is discarded. The organic layer can be washed with 5% aqueous NaOH and then twice with water. The organic layer is filtered and distilled at about <100 Torr (1 Torr~=1 mmHg=133.3 Pa) and about </=58° C. and the distillate is discarded. Into the pot containing this residue is charged 95% EtOH (e.g., 24.0 kg) via a clean filter. The resulting mixture is distilled at about <100 Torr and about </=58° C., the distillate is discarded, and this solvent exchange step is repeated two more times with fresh 95% EtOH. To the pot containing the residue is added 95% EtOH and process water via a filter. The volume of EtOH may be 2.8-5.0 equivalent volumes, where 1 equivalent volume=1 L of EtOH/kg of tasimelteon (unmilled), assuming 90% yield of tasimelteon (unmilled) based on Intermediate 5 (Stage 11) input. In another embodiment, the volume of EtOH may be 3.0-5.0 equivalent volumes. The ratio of EtOH:water may be 0.7:1-1.4:1 (v/v). In another embodiment, the ratio of EtOH: water may be 1.0:1.0. The mixture may be warmed to 35-40° C. and stirred for 30-40 min, cooled to 13-17° C. over a period of 60-120 min, and stirred at 13-17° C. for 60-90 min. If crystallization does not occur, the mixture may be seeded with tasimelteon (unmilled) crystals. Following addition of process water (e.g., 19.2 kg/kg of Intermediate 5 (Stage 11) added over 2-2.5 hr at 10-15° C. followed by stirring at the same temperature for 60-90 min), the precipitate is collected by centrifugation and the cake is analyzed by HPLC to determine if the product meets pre-set specifications, e.g., tasimelteon NLT 99%, Impurities 5 and 6 NMT 0.15% a/a, and other individual impurities NMT 0.10% a/a, e.g., Impurities 1, 2, 3, 4, and 7. Material meeting said pre-set specifications is washed, e.g., with n-heptane, and then dried, e.g., until LOD is NMT 0.7%. The dried material is also analyzed for particle size. Material not meeting the pre-set specifications, e.g., for Impurities 5 and 6 is transferred back to the reaction vessel and recrystallized as described above, i.e., by re-dissolving in warm EtOH:water, filtering, allowing the mixture to cool and crystallize, further precipitating by slow addition of water and collecting by centrifugation. Such re-processed material that meets said impurity specifications is washed, dried and analyzed as described above, after which it is released for milling, discarded, or further re-processed.

The above-described end-step synthesis is illustrative only. For example, other organic solvents or mixtures thereof can be used in place of tert-butyl methyl ether (TBME). Bases other than or in addition to NaOH can also be employed. The solvent for crystallization can be an aqueous solvent, such as an aqueous C1-C4 alcohol, e.g., methanol, ethanol, propanol, isopropanol, n-butanol, sec-butanol, isobutanol, or tert-butanol, or a mixture of organic solvents such as MTBE-EtOH-cyclohexane.

Tasimelteon drug substance is stored as the unmilled drug substance and milled on an as-needed basis, immediately prior to its use in capsule drug product manufacturing. It has been found that use of a jet mill and a dry nitrogen atmosphere is advantageous in achieving uniform particle size with good handling characteristics and minimal loss. Drug substance meeting particle size specifications (e.g., $D_{0.1}$<15 µm (i.e., 10% of the particles are 15 µm in diameter or less); $D_{0.5}$<30 µm; $D_{0.9}$<75 µm for in process and (i) a $D_{90}$ specification set at <105 µm; (ii) a $D_{50}$ specification set at <45 µm; and (iii) a $D_{10}$ specification set at <15 µm for release) is tightly sealed, e.g., in PE bags and/or aluminum bags, e.g., with a dessicant such as a silica dessicant.

When manufacturing pharmaceutical grade tasimelteon, i.e., tasimelteon that is intended for human use, good manufacturing practices (GMP) are employed such as may be required by regulatory bodies in relevant jurisdictions. Bulk pharmaceutical grade tasimelteon is then mixed with excipients to prepare bulk formulated tasimelteon and then formed into an appropriate pharmaceutical dosage form, such as capsules, each comprising 10 mg to 100 mg, e.g., 20 mg, of tasimelteon.

The description above refers to milling. However, the skilled person will recognize that other particle size reduction techniques, e.g., sieving, high shear fluid processing, etc., can also be employed. Similarly, milling techniques other than jet milling, e.g., grinding, cryogenic grinding, cutting or impacting, etc., can also be employed.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What we claim is:

1. A process for preparing a batch of highly purified, pharmaceutical grade tasimelteon, the process comprising:
   (a) analyzing a batch of tasimelteon synthesized under GMP conditions for the presence of one or more of:
      N-(((1R,2R)-2-(2,3-dihydrobenzofuran-4-yl)cyclopropyl)methyl)-3-methylbutanamide (Impurity 1),
      N-(((1R,2R)-2-(2,3-dihydrobenzofuran-4-yl)cyclopropyl)methyl)-pentanamide (Impurity 2),
      1,3-Bis(((1R,2R)-2-(2,3-dihydrobenzofuran-4-yl)cyclopropyl)methyl)urea (Impurity 3),
      N-(((1R,2R)-2-(benzofuran-4-yl)cyclopropyl)methyl) propionamide (Impurity 4)
      N-((2-(2,3-dihydrobenzofuran-4-yl)-1-((2-(2,3-dihydrobenzofuran-4-yl)cyclopropyl)(propionamido) methyl) cyclopropyl)methyl)propionamide (Impurity 5),
      2-hydroxy-6-(2-(propionamidomethyl)cyclopropyl) phenethyl 2-(2-hydroxyethyl)-3-(2-(propionamidomethyl)cyclopropyl)phenyl carbonate (Impurity 6),
      N-(((1R,2R)-2-(3-Oxo-2,3-dihydrobenzofuran-4-yl) cyclopropyl)methyl)propionamide (Impurity 7)
   and
   (b) if the batch meets pre-set specifications for the amount of the one or more of Impurity 1, Impurity 2, Impurity 3, Impurity 4, Impurity 5, Impurity 6, or Impurity 7, then continuing to process the tasimelteon to prepare bulk tasimelteon drug substance for formulation or
   (c) if the tasimelteon does not meet said pre-set specifications, then further purifying (such as by recrystallization, trituration, extraction, or chromatography) the tasimelteon and repeating steps (a) and (b) or discarding the batch,
      wherein the step (b) processing of tasimelteon comprises reducing the tasimelteon particle size to meet particle size specifications.

2. The process of claim 1, wherein the particle size specifications comprise one or more specification selected from a group consisting of: (i) a D90 specification set at less than about 105 µm; (ii) a D50 specification set at less than about 45 µm; and (iii) a D10 specification set at less than about 15 µm.

3. The process of claim 2, wherein the step (b) processing of tasimelteon further comprises admixing the milled tasimelteon with one or more pharmaceutically acceptable excipients to prepare tasimelteon bulk drug substance.

4. The process of claim 3, wherein the admixed tasimelteon is prepared for use in a pharmaceutical composition in pharmaceutical dosage units for human use.

5. The process of claim 1, wherein the batch of tasimelteon that is analyzed in step (a) is synthesized by allowing ((1R,2R)-2-(2,3-dihydrobenzofuran-4-yl)cyclopropyl) methanaminium chloride (Intermediate 5) to come in contact and react with propionyl chloride in the presence of an organic solvent and a base.

6. The process of claim 5, wherein the tasimelteon synthesized by contacting and reacting ((1R,2R)-2-(2,3-dihydrobenzofuran-4-yl)cyclopropyl) methanaminium chloride (Intermediate 5) with propionyl chloride in the presence of the base is then, prior to the step (a) analysis, prepared in crystalline form by filtering the reaction mixture to prepare a filtrate comprising the tasimelteon and then crystallizing the tasimelteon in a solvent.

7. The process of claim 6, wherein the solvent for the crystallization of tasimelteon is an aqueous alcohol.

8. The process of claim 1, wherein the solvent for the recrystallization of the tasimelteon is an aqueous alcohol.

9. The process of claim 5, wherein the organic solvent is TBME and the base is NaOH.

10. The process of claim 6, wherein (i) the filtrate, prior to crystallizing, is concentrated by distillation, (ii) an alcohol is added, (iii) the residue/alcohol mixture is concentrated by distillation, (iv) the residue is dissolved in an aqueous alcohol, (v) the tasimelteon is crystallized from the alcohol/water solution, and (vi) the tasimelteon crystals are collected for the step (a) analysis.

11. The process of claim 10, wherein the step (c) recrystallization, if necessary, is carried out by subjecting the tasimelteon that failed to meet the pre-set specifications to steps (iv), (v), and (vi).

12. The process of claim 10, wherein the crystallization step (v) is facilitated by seeding.

* * * * *